United States Patent [19]

Bolich, Jr. et al.

[11] Patent Number: 4,472,297
[45] Date of Patent: Sep. 18, 1984

[54] SHAMPOO COMPOSITIONS CONTAINING HYDROXYPROPYL GUAR GUM

[75] Inventors: Raymond E. Bolich, Jr., Maineville, Ohio; Robert R. Schmidt, Ft. Wright, Ky.

[73] Assignee: The Procter & Gamble Company, Cincinnati, Ohio

[21] Appl. No.: 532,246

[22] Filed: Sep. 14, 1983

Related U.S. Application Data

[63] Continuation of Ser. No. 353,121, Mar. 1, 1982, abandoned, which is a continuation-in-part of Ser. No. 256,873, Apr. 24, 1981, abandoned.

[51] Int. Cl.$^3$ .......................... C11D 1/14; C11D 3/22
[52] U.S. Cl. .............................. 252/531; 252/174.17; 252/532; 252/550; 252/551; 252/DIG. 2; 252/DIG. 13; 252/DIG. 14
[58] Field of Search .................. 252/89.1, 173, 174.17, 252/174.23, 550, 551, DIG. 2, DIG. 13, DIG. 14, 531, 532; 424/70

[56] References Cited

U.S. PATENT DOCUMENTS

| 3,658,985 | 4/1972 | Olson et al. ........................... 424/70 |
| 3,697,644 | 10/1972 | Laiderman . |
| 3,748,201 | 7/1973 | Jordan . |
| 3,928,251 | 12/1975 | Bolich et al. ........................ 252/545 |
| 3,932,610 | 1/1976 | Rudy et al. . |
| 3,960,782 | 6/1976 | Daley et al. ......................... 252/544 |
| 4,031,306 | 6/1977 | De Martino et al. . |
| 4,061,602 | 12/1977 | Oberstar et al. ..................... 252/547 |
| 4,126,674 | 12/1978 | Mausner ................................ 424/31 |
| 4,140,759 | 2/1979 | Mausner ................................ 424/70 |
| 4,260,528 | 6/1979 | Fox et al. ............................ 252/525 |
| 4,330,438 | 5/1982 | Dierassi et al. ..................... 252/552 |
| 4,414,144 | 11/1983 | Liebowitz et al. .................. 252/548 |

FOREIGN PATENT DOCUMENTS 911214  11/1962  United Kingdom .

OTHER PUBLICATIONS

Polymers for Personal Care Products, Clear Shampoo, Celanese Plastics & Specialties Co., Application Bulletin.
Polymers for Personal Care Products, "Comparative Performance of Jaguar ®HP-60 Versus Hydroxypropyl Methylcellulose", Celanese Plastics & Specialties Company.

*Primary Examiner*—Prince E. Willis
*Attorney, Agent, or Firm*—Richard C. Witte; John V. Gorman; Douglas C. Mohl

[57] ABSTRACT

Shampoo compositions which are cosmetically attractive, stable and which also have excellent performance properties. The compositions contain a hydroxypropyl guar gum, an alcohol, a surfactant, water and an electrolyte as essential components.

11 Claims, No Drawings

SHAMPOO COMPOSITIONS CONTAINING HYDROXYPROPYL GUAR GUM

CROSS REFERENCE TO RELATED APPLICATION

This is a continuation application of application Ser. No. 353,121, filed Mar. 1, 1982 now abandoned, which is a continuation-in-part application of application Ser. No. 256,873, filed Apr. 24, 1981, now abandoned.

TECHNICAL FIELD

The present invention is related to shampoo compositions which contain a hydroxypropyl guar gum as a thickening/conditioning aid.

BACKGROUND ART

The use of polymeric gums including guar gums, in shampoo compositions is well known. U.S. patents disclosing such compositions are U.S. Pat. No. 3,650,985, Apr. 25, 1972 to Olson et al; U.S. Pat. No. 3,697,644, Oct. 10, 1972 to Laiderman, U.S. Pat. No. 3,932,610, Jan. 13, 1976 to Rudy et al; U.S. Pat. No. 4,031,306, June 21, 1977 to DeMartino et al; and U.S. Pat. No. 4,061,602, Dec. 6, 1977 to Oberstar et al. See also Celanese Plastics & Specialties Company Trade Bulletin.

While it is known to use polymeric gums in shampoos there is no teaching or suggestion of the problems encountered with hydroxypropyl guar gums in making stable, good performing shampoo compositions or solutions thereto.

Specifically, there are no suggestions for incorporating an alcohol and electrolytes into such compositions to obtain satisfactory products.

It is, therefore, an object of the present invention to provide hydroxypropyl guar gum containing shampoos which are stable and cosmetically attractive.

It is a further object of the present invention to provide shampoos which are clear as well as stable.

It is still a further object of the present invention to provide shampoos which deliver good hair condition.

These and other objects of the present invention will become obvious from the detailed description which follows.

DISCLOSURE OF THE INVENTION

The present invention relates to shampoo compositions comprising from about 0.1% to about 1.5% of a hydroxypropyl guar gum, from about 0.5% to about 20% of an alcohol containing from about 1 to about 4 carbon atoms and about 1 to about 3 hydroxy groups, from about 10% to about 50% of a surfactant, from about 0.1% to about 7% total electrolyte level and from about 50% to about 95% of water.

DETAILED DESCRIPTION OF THE INVENTION

Hydroxypropyl Guar Gum

The hydroxypropyl guar gums useful in the compositions of the present invention may be formed by reacting propylene oxide with guar gum. Such a process is described in U.S. Pat. No. 3,748,201, Oct. 8, 1971 to Jordan, incorporated herein by reference.

Guar gum is naturally occurring in the seed of the guar plant and is a high molecular weight carbohydrate polymer or polysaccharide made up of mannose and galactose units linked together. The guar molecule is essentially a straight chain of mannose units linked to each other by means of beta (1-4) glycosidic linkages. Galactose units branch from alternate mannose units through alpha (1-6) linkages with the mannose units.

In the guar gum molecule, each mannose and galactose unit has from 2-4 hydroxyl groups, averaging 3, depending on where it is located in the polymer chain. Guar gum derivatives are produced by reacting guar gum such that substitution of chemical moities occurs on some of these hydroxyl units. Hydroxypropyl guar gums are a family of materials with hydroxypropyl groups substituted for some of the hydroxyl units. The term "molar substitution" is used to indicate the average number of hydroxypropyl units occurring on any single ring of the polymer molecule. It is preferred that the hydroxypropyl guar gum used in the present invention have a molar substitution of about 0.1 to about 1.0, preferably from about 0.4 to about 0.9.

Suitable hydroxypropyl guar gums are offered by Celanese Plastics & Specialties Company under the name Jaguar ®. A preferred material is Jaguar ®HP-60 having molar substitution of about 0.6.

The amount of hydroxypropyl guar gum found useful in the present compositions is from about 0.1% to about 1.5%, preferably from about 0.6% to about 1.0%.

Alcohol

A second essential component of the present compositions is an alcohol containing from about 1 to about 4 carbon atoms and from about 1 to about 3 hydroxyl groups.

Preferably the number of carbon atoms is from about 2 to about 3 while the number of hydroxyl groups is from about 1 to about 2. The alcohol is present at a level of from about 0.5% to about 20%, preferably from about 1% to about 6% in the instant compositions.

Examples of suitable alcohols are ethanol, methanol, propanol, isopropanol, glycerin and ethylene glycol. The most preferred alcohol is ethanol.

Surfactant

The third essential component of the present compositions is a surfactant. The surfactant, which may be selected from any of a wide variety of anionic (soap and nonsoap), amphoteric, zwitterionic, nonionic and, in certain instances, cationic surfactants, is present at a level of from about 10% to about 50%, preferably from about 10% to about 20%.

Examples of suitable soaps are the sodium, potassium, ammonium and alkanol ammonium salts of higher fatty acids (those having 10-20 carbon atoms).

Anionic nonsoap surfactants can be exemplified by the alkali metal salts of organic sulfuric reaction products having in their molecular structure an alkyl radical containing from 8-22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$-$C_{18}$ carbon atoms), sodium oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and other known in the art.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g. Tween 20-polyoxyethylene (20) sorbitan monolaurate.

4. Long chain tertiary amine oxides corresponding to the following general formula:

$$R_1R_2R_3N \to O$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyldecylamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$$RR'R''P \to O$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are:
dodecyldimethylphosphine oxide,
tetradecyldimethylphosphine oxide,
tetradecylmethylethylphosphine oxide,
3,6,9-trioxaoctadecyldimethylphosphine oxide,
cetyldimethylphosphine oxide,
3-dodecoxy-2-hydroxypropyldi(2-hydroxyethyl) phosphine oxide,
stearyldimethylphosphine oxide,
cetylethylpropylphosphine oxide,
oleyldiethylphosphine oxide,
dodecyldiethylphosphine oxide,
tetradecyldiethylphosphine oxide,
dodecyldipropylphosphine oxide,
dodecyldi(hydroxymethyl)phosphine oxide,
dodecyldi(2-hydroxyethyl)phosphine oxide,
tetradecylmethyl-2-hydroxypropylphosphine oxide,
oleyldimethylphosphine oxide,
2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include:
octadecyl methyl sulfoxide,
2-ketotridecyl methyl sulfoxide,
3,6,9-trioxaoctadecyl 2-hydroxyethyl sulfoxide,
dodecyl methyl sulfoxide,
oleyl 3-hydroxypropyl sulfoxide,
tetradecyl methyl sulfoxide,
3-methoxytridecyl methyl sulfoxide,
3-hydroxytridecyl methyl sulfoxide,
3-hydroxy-4-dodecoxybutyl methyl sulfoxide.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

$$R^2-Y^{(+)}(R^3)_x-CH_2-R^4-Z^{(-)}$$

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3[P,P-diethyl-P-3,6,9-trioxatetradexocylphosphonio]-2-hydroxypropane-1-phosphate;
3-]N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-(P,P-dimethyl-P-dodecylphosphonio)-propane-1-phosphonate; and
5-[N,N-di(3-hydroxypropyl)-N-hexadecylammonio]-2-hydroxypentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl, betaine, lauryl dimethyl carboxymethyl betaine, lauryl dimethyl alpha-carboxy-ethyl betaine, cetyl dimethyl carboxymethyl betaine, lauryl bis-(2-hydroxy-ethyl)carboxy methyl betaine, stearyl bis-(2-hydroxy-propyl) carboxymethyl betaine, oleyl dimethyl gamma-carboxypropyl betaine, lauryl bis-(2-hydroxypropyl)alpha-carboxyethyl betaine, etc. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amido betaines and amidosulfobetaines, wherein the $RCONH(CH_2)_3$ radical is attached to the nitrogen atom are also useful in this invention.

Many cationic surfactants are known to the art. By way of example, the following may be mentioned:
stearyldimethylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride;
laurylpyridinium chloride;
laurylisoquinolium bromide;
ditallow(hydrogenated)dimethyl ammonium chloride;
dilauryldimethyl ammonium chloride; and
stearalkonium chloride.

Many additional nonsoap surfactants are described in McCutcheon's, Detergents and Emulsifiers, 1979 Annual, published by Allured Publishing Corporation, which is incorporated herein by reference.

The above-mentioned surfactants can be used alone or in combination in the shampoo compositions of the present invention. The anionic surfactants, particularly the alkyl sulfates, the ethoxylated alkyl sulfates and mixtures thereof are preferred.

Electrolyte

An additional requirement of the present compositions is that they contain a certain level of electrolyte. The electrolyte may be added as a separate ingredient or be present in total or in part with the surfactant or another ingredient. Suitable electrolytes include inorganic salts (e.g. sodium chloride) as well as organic salts (e.g. sodium citrate). The amount of electrolyte varies with the type of surfactant but is generally present at a level of from about 0.1% to about 7%, preferably from about 0.2% to about 4%. The surfactant salts themselves are not included in the present electrolyte definition but other salts are. In addition to the above-mentioned chloride and citrate salts, other salts include phosphates, sulfates and other halogen ion salts. The counter ions of such salts can be sodium or other monovalent cations as well as di and tri valent cations. It is recognized that these salts may serve as thickening aids or buffering aids in addition to their role in making the present compositions satisfactory in other ways.

Aqueous Carrier

The shampoos herein are in the form of liquids in which water is the principal diluent. The level of water in the compositions is typically from about 50% to about 95%, preferably from about 70% to about 85%.

Optional Components

The shampoos herein can contain a variety of nonessential optional ingredients suitable for rendering such compositions more desirable. Such conventional optional ingredients are well known to those skilled in the art, e.g., preservatives such as benzyl alcohol, methyl paraben, propyl paraben and imidazolidinyl urea; other thickeners and viscosity modifiers such as $C_8$–$C_{18}$ ethanol amide (e.g. coconut ethanol amide), carboxymethyl cellulose, methylcellulose and polyvinyl alcohol; pH adjusting agents such as citric acid, succinic acid, phosphoric acid, sodium hydroxide, etc.; suspending agents such as magnesium/aluminum silicate; perfumes; dyes; and, sequestering agents such as disodium ethylenediamine tetraacetate.

One preferred form of the present compositions is a clear product. However, if desired, an opacifier such as ethylene glycol distearate or talc may be used to give the product a pearlescent effect.

If present, the optional components individually generally comprise from about 0.001% to 10.0% by weight of the composition. The pH of the shampoos herein is generally from about 3 to about 9, preferably from about 6 to about 8, and have a viscosity of from about 1000 cps to about 6000 cps.

METHOD OF MANUFACTURE

The shampoo compositions of the present invention may be made using techniques well known in the art. A suitable method is shown in Example 1.

INDUSTRIAL APPLICABILITY

The shampoos herein are useful in shampooing human hair in the conventional manner. They may also be used as a cleansing aid for the entire body.

The following Examples further describe and demonstrate the preferred embodiments within the scope of the present invention. The Examples are given solely for the purpose of illustration and are not to be construed as limitations of the present invention as many variations thereof are possible without departing from its spirit and scope. Unless otherwise indicated, all percentages and ratios herein are by weight.

EXAMPLE I

| | |
|---|---|
| Clindrol Superamide 100 CG[1] (coconut diethaolamide) | 3.50% |
| Jaguar HP-60[2] (hydroxypropyl guar gum) | 0.70 |
| Sodium Lauryl Sulfate Solution (27%)* | 16.63 |
| Ammonium Lauryl Sulfate Solution (27%)* | 33.25 |
| Perfume | 1.00 |
| Ethanol, 190 proof | 3.00 |
| Kathon CG[3] (1.5% active solution) | 0.03 |
| Monosodium Phosphate | 1.20 |
| Disodium Phosphate | 0.32 |
| Sodium Chloride | 0.20 |
| Distilled Water q.s. | 100.00% |

[1]Supplied by Clintwood Chemical Company.
[2]Supplied by Celanese Plastics and Specialties Company.
[3]Supplied by Rohm & Haas.
*These solutions together, provide 0.17% sodium chloride and 0.28% sodium sulfate.

The above composition was prepared by dispersing 7 grams of Jaguar HP-60 in 30 grams of 190 proof ethanol and 35 grams of Clindrol Superamide 100 CG with a Lightnin ® Mixer. The remaining ingredients were added in the following order: Distilled water, monosodium phosphate, disodium phosphate, sodium chloride, sodium lauryl sulfate solution, ammonium lauryl sulfate solution, Kathon CG, and perfume.

EXAMPLE II

The following composition of the present invention was prepared in a manner similar to that described in Example I.

| | |
|---|---|
| Lauric Diethanolamide Solution (50%) | 5.00% |
| Jaguar HP-60 (hydroxypropyl guar gum) | 1.00 |
| Monosodium phosphate | 1.15 |
| Disodium phosphate | 0.32 |
| Perfume | 1.00 |
| Kathon CG[2] (1.5% active solution) | 0.03 |
| Hydrochloric acid, conc. | 0.75 |
| Sodium Lauryl Sulfate Solution (27%)* | 16.63 |
| Ammonium Lauryl Sulfate Solution (27%)* | 33.25 |
| Ethanol, 190 proof | 8.00 |
| Distilled Water q.s. | 100.00% |

[1]Supplied by Celanese Plastics and Specialties Company.
[2]Supplied by Rohm & Haas.
*These solutions together provide 0.17% sodium chloride and 0.28% sodium sulfate.

EXAMPLE III

The following composition of the present invention was prepared in a manner similar to that described in Example I.

| Formula | % |
|---|---|
| Sodium Lauryl Ethoxy (3) Sulfate Solution (27%)* | 39.2 |
| Sodium Lauryl Sulfate Solution (27%)* | 32.7 |
| Coconut Monoethanol Amide | 4.0 |
| Perfume | 2.0 |
| Ethanol, 190 Proof | 6.0 |
| Ethylene Glycol Distearate | 1.0 |
| Disodium Ethylene Diamine Tetraacetate | 0.10 |
| Preservatives | 0.25 |
| Citric Acid | 0.29 |
| Color | 0.43 |
| Jaguar HP-60[1] (hydroxypropyl guar gum) | 0.65 |
| Water | Balance |
| | 100.00 |

[1]Supplied by Celanese Plastics and Specialties Company.
*These solutions together provide 0.35% sodium chloride and 0.11% sodium sulfate.

EXAMPLE IV

| | |
|---|---|
| Aerosol 30[1] (cocoamidopropyl betaine) solution - 30%)* | 40.00% |
| Ethanol, 190 proof | 15.00 |
| Jaguar HP-11[2] (hydroxypropyl guar gum) | 0.50 |
| Perfume | 1.00 |
| Distilled Water q.s. | 100.00% |

[1]Supplied by American Cyanamid.
[2]Supplied by Celanese.
*The betaine solution provides 2.5% sodium chloride.

The above composition was prepared by dispersing 5 grams of Jaguar HP-11 in 150 grams of 190 proof ethanol with a Lightnin ® mixer. The Aerosol 30 was then added, followed by distilled water. The perfume was added last.

What is claimed is:

1. A liquid shampoo comprising:
   (a) from about 0.1% to about 1.5% of a hydroxypropyl guar gum;
   (b) from about 0.5% to about 20% of an alcohol containing from about 1 to about 4 carbon atoms and from 1 to about 3 hydroxy groups;
   (c) from about 10% to about 50% of a synthetic anionic surfactant selected from the group consisting alkyl sulfates, ethoxylated alkyl sulfates and mixtures thereof;
   (d) from about 0.1% to about 7% of an electrolyte; and
   (e) from about 50% to about 95% water.

2. A shampoo according to claim 1 wherein the hydroxypropyl guar gum has a molar substitution of from about 0.1 to about 1.0.

3. A shampoo according to claim 2 wherein the alcohol is selected from the group consisting of ethanol, methanol, propanol, isopropanol, glycerin, ethylene glycol and mixtures thereof.

4. A shampoo according to claim 3 wherein the electrolyte is selected from the group consisting of sodium sulfate, sodium chloride, ammonium chloride, monosodium phosphate, disodium phosphate, and mixtures thereof.

5. A shampoo according to claim 4 wherein the surfactant is selected from the group consisting of sodium alkyl sulfate, ammonium alkyl sulfate, sodium ethoxy(3) alkyl sulfate and mixtures thereof.

6. A shampoo according to claim 5 which in addition contains an alkanolamide of a fatty acid having from about 8 to about 18 carbon atoms.

7. A shampoo according to claim 6 wherein the hydroxy propyl guar gum is present at a level of from about 0.6% to about 1.0%.

8. A shampoo according to claim 7 wherein the alcohol is ethanol and is present at a level of from about 1% to about 6%.

9. A shampoo according to claim 8 wherein the surfactant is present at a level of from about 10% to about 20%.

10. A shampoo according to claim 9 wherein the hydroxypropyl guar gum has a molar substitution of from about 0.4 to about 0.9.

11. A shampoo according to claim 10 which in addition contains from about 0.1% to about 10% of an opacifier selected from the group consisting of ethylene glycol distearate, talc and mixtures thereof.

* * * * *